United States Patent [19]
Wagner et al.

[11] 3,971,736
[45] July 27, 1976

[54] CATHEPSIN IN D INHIBITORS

[75] Inventors: Arthur F. Wagner, Princeton, N.J.;
Frederick W. Holly, Glenside, Pa.;
Tsau-Yen Lin, Piscataway;
Tsung-Ying Shen, Westfield, both of
N.J.; Ralph F. Hirschmann, Blue
Bell, Pa.

[73] Assignee: Merck & Co., Inc., Rahway, N.J.

[22] Filed: Jan. 21, 1975

[21] Appl. No.: 542,884

[52] U.S. Cl. .......................... 260/112.5 R; 424/177
[51] Int. Cl.² .................. C07C 103/52; A61K 37/00
[58] Field of Search ................... 260/112.5; 424/177

[56] References Cited
UNITED STATES PATENTS

| | | | |
|---|---|---|---|
| 3,819,486 | 6/1974 | Murao et al. | 260/112.5 R |
| 3,840,513 | 10/1974 | Umezawa et al. | 260/112.5 R |
| 3,840,516 | 10/1974 | Umezawa et al. | 260/112.5 R |
| 3,867,364 | 2/1975 | Umezawa et al. | 260/112.5 R |
| 3,869,347 | 3/1975 | Umezawa et al. | 260/112.5 R |
| 3,878,185 | 4/1975 | Murao et al. | 260/112.5 R |
| 3,885,012 | 5/1975 | Tschesche et al. | 260/112.5 R |

OTHER PUBLICATIONS

J. M. Stewart and J. D. Young, "Solid Phase Peptide Synthesis," Freeman and Co., San Francisco, 1969, pp. 1–26.

Keilova et al., Biochim. Biophys. Acta, 284, 461–464 (1972).

*Primary Examiner*—Lewis Gotts
*Assistant Examiner*—Reginald J. Suyat
*Attorney, Agent, or Firm*—Mario A. Monaco; Harry E. Westlake, Jr.

[57] ABSTRACT

Hexa- and heptapeptides of formula W-[X-Pro-Phe-Phe-Y-Z]$_n$H prepared by standard synthetic peptide techniques are anti-inflammatory, anti-rheumatoid arthritic and anti-ulcer agents.

10 Claims, No Drawings

CATHEPSIN IN D INHIBITORS

This invention is concerned with novel hexa- and heptapeptides and dimers and trimers of the hexapeptides; processes for their preparation; their utilities as anti-inflammatory, anti-rheumatoid arthritic and anti-ulcer; and pharmaceutical compositions comprising the novel peptides as the active ingredient.

More particularly, this invention is concerned with novel hexa- and heptapeptides of general structural formula:

W[X-Pro-Phe-Phe-Y-Z]H$_n$ or pharmaceutically acceptable salt thereof; wherein
 $n$ is 1, 2, or 3,
 W is hydrogen, acyl, or glycosyl,
 X and Z are the same or different and each is the D-isomer of a natural mammalian α-amino acid, and
 Y is a natural mammalian L-α-amino acid.

The group, W, in the above generic formula has been defined as hydrogen, acyl, or glycosyl. When it is acyl or glycosyl, it may function as a protecting or blocking group for the α-amino function of the amino acid, X. It is not essential to the utility of these novel peptides that the terminal amino group be blocked, but it does aid in prolonging the metabolic half-life of the active peptide and promoting pharmacological distribution. Consequently, although W can be hydrogen, acyl, or glycosyl, it is preferred that it be acyl or glycosyl and most preferably, acyl.

The type of acyl group is not critical and can be either carboxyl or sulfonyl; contain up to 25 carbons; be aliphatic, aliphaticoxy, cycloaliphatic, aromatic, or heterocyclic; and carry a variety of functional groups such as amino,di(alkyl)amino, carbonyl, or hydroxyl. For example, W can be an amino acid residue in either the D or L configuration, such as pyroglutamyl (Pyroglu), prolyl (Pro), valyl (Val), glycyl (Gly), or the like giving rise to the heptapeptides of this invention and exemplifying a heterocyclic acyl, an aliphatic acyl and amino and carbonyl functional groups.

The nitrogen heterocycle need not be part of an α-amino acid such as proline or pyroglutamic acids, but may also be such as indole-3-acetyl or the like.

The aliphatic moiety may in addition be one from a simple fatty acid such as isovaleric acid, or the like.

An example of an aromatic residue and a sulfonyl acyl is 5-dimethylaminonaphthalene-1-sulfonyl (Dansyl).

The acyl group may in addition be a glycuronic acid residue such as D-glucuronyl or the like, exemplifying the presence of hydroxyl functional groups.

The utility of an aliphiticoxy residue is exemplified by t-butyloxycarbonyl or the like.

In addition, the acyl group, W, may be derived from a steroidal acid such as cholic acid.

The most preferred glycosyl as the N-terminal group, W, is 2-deoxy-2-acetamidoglucopyranosyl.

In the more preferred aspects of this invention, W is an α-amino acyl or a C$_{1-5}$ alkoxycarbonyl group, and preferably pyroglutamyl or t-butyloxycarbonyl.

The variable, X, in the generic formula of the novel compounds of this invention has been defined as the D-isomer of a naturally occurring mammalian α-amino acid. In a preferred embodiment, X is selected from D-aromatic α-amino acids or D-aliphatic α-amino acids and, in the most preferred aspects, is D-phenylalanine (DPhe) or D-leucine (DLeu).

The third variable component of the novel compound of this invention is Y and is defined as a natural mammalian L-α-amino acid. In the more preferred aspects of the invention, Y is a cyclic α-amino acid or an aliphatic α-amino acid and most preferably is L-proline or L-valine.

The terminal amino acid, Z, is also the D-isomer of a natural mammalian α-amino acid and is preferably selected from D-leucine, D-tryptophan (DTryp), D-phenylalanine, D-norleucine (DNle), D-allo-i-leucine (D-allo i-Leu), D-alanine (DAla), D-proline (DPro), and D-valine. In the most preferred aspects of the invention, Z represents D-leucine, D-tryptophan, D-phenylalanine, or D-norleucine.

The pharmaceutically acceptable salts of the novel compounds of this invention comprise acid addition salts of free amino functions and salts of free carboxylic acid residues. The acid addition salts are those derived from acids commonly employed in the pharmaceutical industry and are principally from mineral acids such as hydrochloric, hydrobromic, sulfuric, nitric or the like. The carboxylic acid salts are those derived from alkali metal hydroxides, such as sodium and potassium salts.

The novel peptides of this invention are prepared by standard techniques in the art of peptide chemistry and involve either the "solid phase" method developed by Merrifield, or "solution methods". In either methodology, the peptides are ultimately synthesized by stepwise formation of amide bonds between successive amino acids. The actual order in which the bonds are formed, however, can in some instances be varied to suit the particular needs or convenience of the investigator.

In the solid phase method, the desired peptide can be obtained by building it up one amino acid at a time starting with the C-terminal amino acid. A commercially available derivatized polymer such as chlormethylated styrene-2% divinylbenzene copolymer is suspended in an anhydrous peroxide free ether, such as tetrahydrofuran, tetrahydropyran, dioxane, 1,2-dimethoxy-ethane, or the like. A stoichiometric equivalent of an N-acylated α-amino acid is added thereto, and the mixture is heated for 12–36 hours at 40°C. to reflux temperature in the presence of an acid acceptor, such as an organic base, for example triethylamine or pyridine. The N-acyl group on the α-amino acid nitrogen can be any of a number of such acyl moieties commonly employed in peptide chemistry such as t-butyloxycarbonyl, carbobenzyloxy, or the like. After the reaction is complete, the polymer bound N-acylated α-amino acid is washed, isolated by filtration, dried and assayed for amino acid content.

The polymer-bound N-acylated α-amino acid is then suspended in an ether type solvent, preferably dioxane, and after equilibration, treated with a dilute anhydrous mineral acid, preferably hydrochloric acid in dioxane, containing in certain instances about 2% mercaptoethanol, to remove the N-acyl group. After a series of washings, neutralization of the amino function and additional washing, it is treated with an excess of another N-acyl α-amino acid and a corresponding excess of dicyclohexylcarbodiimide. After 1 to 3 hours at room temperature to about 35°C., the polymer-bound N-acyl dipeptide is washed and may be isolated or used for successive condensations without isolation.

By repeating the above steps employing α-amino acids in the appropriate sequence, there is produced the desired polymer-bound peptide, with or without the N-protecting group.

There are several methods available for separating the peptide from the polymer.

A common method where a free carboxyl group is required on the terminal amino acid, and certain susceptible amino acid residues are absent, is to suspend the polymer-bound peptide in cool trifluoroacetic acid and bubble anhydrous hydrogen bromide through the suspension for 0.5 to 3 hours at a temperature of 10°–30°C., conveniently room temperature. The desired peptide is isolated by filtration, and concentration of the filtrate to dryness. This procedure will also hydrolyze certain common N-blocking groups.

Another method particularly useful for liberating peptides containing susceptible amino acids mentioned above, is to suspend the polymer-bound peptide in a $C_{1-3}$ alkanol, preferably methanol, containing a small amount of a strong organic base such as tri($C_{1-3}$ alkyl)-amine, preferably triethylamine, and stir the mixture at 10°–30°C., preferably room temperature, for 10–24 hours. After filtration of the mixture and concentration of the filtrate to dryness, there is obtained the $C_{1-3}$ alkyl ester of the desired peptide.

Esters, obtained as described above, are useful as C-terminal blocking groups where it is desired to perform further chemical modification at some other point in the peptide chain. Alternatively, the free peptide is obtained from the ester by saponification with dilute aqueous sodium hydroxide, usually in a $C_{1-3}$ alkanolic solution, preferably methanolic.

A third method for eliminating the polymer from the synthetic peptide is to suspend the polymer-bound peptide in a solvent such as N,N-dimethylformamide, dimethyl sulfoxide, or dimethylsulfone, add excess anhydrous hydrazine at 15°–30°C., preferably room temperature, and agitate for 1 to 4 hours. After filtration and concentration to dryness there is obtained the hydrazide of the desired peptide.

Hydrazides obtained in this manner are useful intermediates where it is desired to add an amino acid or peptide to the C-terminal end. The hydrazide is dissolved in an inert organic solvent such as N,N-dimethylformamide and cooled to −10° to −30°C. After acidification to pH 1–2 with an anhydrous dilute mineral acid such as hydrochloric acid in an ether such as tetrahydrofuran, the solution is treated portionwise with isoamyl nitrite until a small excess of nitrite persists, thus producing the corresponding acid azide. The acid azide is then condensed with an α-amino acid or peptide in which the C-terminal carboxyl group is protected as an ester, such as a $C_{1-3}$ alkyl ester or as a polymer ester as described previously. The free C-terminal carboxyl group is then liberated as described above.

Carboxylic acid derivatives, other than the azide, such as acid halides and anhydrides can also be employed as acylating agents in much the same manner as described for the azide. These derivatives are also useful for the synthesis of peptide analogs containing acid labile N-terminal groups, W. Dicyclohexylcarbodiimide is, of course, also a useful condensing agent for acylation purposes, particularly where the acyl halides are not readily available.

The N-terminal glycosyl analogs of these peptides are prepared by treating the polymer-bound peptide or a peptide ester with an acylated glycosyl halide in the presence of a tertiary amine followed by selective removal of the acyl protecting groups of the glycosyl moiety.

The novel compounds of this invention may also be prepared by a variety of techniques not involving the use of a solid support. These so-called solution-methods for peptide synthesis generally involve a condensation in solution between an N-blocked carboxyl activated α-amino acid and a carboxyl blocked α-amino acid. For example, the α-amino acid to serve as the C-terminal moiety of a given sequence may be converted to the corresponding alkyl ester and then condensed with an N-blocked α-amino acid that will occupy the penultimate position to the C-terminal end. The carbobenzyloxy and t-butyloxycarbonyl groups are among the more popular groups used for protecting the amino group. The condensation in solution may be effected by using an appropriate carbodiimide or alternatively, the carbonyl function of the N-protected α-amino acid component of the condensation reaction may be activated by a variety of other methods including the formation of an activated ester such as the p-nitrophenyl ester. Other solution methods involving starting with the N-terminal moiety or with smaller polypeptide components of the desired analogs are also feasible starting points for the synthesis of this class of compounds by solution techniques.

The solid phase and solution methods are not really different chemically but differ principally in techniques employed in isolation and purification of intermediates and final products. The solid phase techniques generally facilitate these manipulations.

In a degenerative disease such as rheumatoid arthritis, joint tissue degradation is the major cause of irreversible deformation. This tissue erosion is mainly a consequence of the action of tissue hydrolytic enzyme systems regardless of etiology and disease mediating systems. Among cartilage lytic enzyme systems, Cathepsin D is uniquely important since the enzyme is a dominant proteinase in tissue (lysosomes) and is released extracellularly upon receiving stimuli, and has the capacity to hydrolyze complex proteins. It has now been discovered that the novel compounds of this invention are potent inhibitors of the proteolytic enzyme, Cathepsin D. They are therefore useful in preventing the progress of tissue degeneration in diseases such as rheumatoid arthritis and related inflammatory diseases.

In addition to being inhibitors of Cathepsin D, the novel compounds are anti-inflammatory as measured by the well known rat foot edema assay.

For these purposes the compounds of the invention may be administered to humans and other warm-blooded animals orally, topically, parenterally, by inhalation spray or rectally in dosage unit formulations containing conventional pharmaceutically acceptable carriers, adjuvants and vehicles. The term parenteral as used herein includes subcutaneous injections, intravenous, intra-muscular, intra-articular, and intrasternal injection or infusion techniques.

The pharmaceutical compositions containing the active ingredient may be in a form suitable for oral use, for example, as enteric coated tablets, troches, lozenges, aqueous or oily suspensions, dispersible powders or granules, emulsions, or hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example for sorbitan mono-oleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the active agents are employed.

Dosage levels of the order of 0.1–140 mg./kg/day are useful in the novel method of treatment of this invention but will usually be in the range of 0.5–50 mg./kg/day and preferably from 1 to about 15 mg./kg./day.

The amount of active ingredient that may be combined with the carrier materials to produce a single dosage form will vary depending upon the host treated and the particular mode of administration. For example, a formulation intended for the oral administration of humans may contain from 5 mg. to 5 gm. of active agent compounded with an appropriate and convenient amount of carrier material which may vary from about 5 to about 95 percent of the total composition.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of this invention also find utility as inhibitors of the enzyme, pepsin, and are therefore of use in the treatment of peptic ulcer in humans and other animals, particularly swine, and may be administered at the same dosage rate as described above for this purpose.

EXAMPLE 1

Pyroglu-DPhe-Pro-Phe-Phe-Val-DTrp

Step A: Preparation of Polymer-Bound t-butyloxycarbonyl D-tryptophan

Twenty grams of chloromethylated styrene-2% divinylbenzene copolymer (1.94 meq Cl/g; 38.4 meq) was suspended in 150 ml. of anhydrous, peroxide-free tetrahydrofuran and stirred while a solution of 11.68 g (38.4 meq) of t-butyloxycarbonyl D-tryptophan in 50 ml. of anhydrous, peroxide-free tetrahydrofuran was added. After the mixture was stirred for 1 hour at room temperature, 4.84 ml. (34.6 mmoles) of triethylamine was added, and the mixture was heated under gentle reflux for 24 hours.

The polymer-bound t-butyloxycarbonyl D-tryptophan was isolated by filtration and washed for 5 minutes with 3 × 100 ml. of tetrahydrofuran; 3 × 100 ml. of ethanol; 1 × 100 ml. of acetic acid; 3 × 100 ml. of water; 3 × 100 ml. of methanol; and 3 × 100 ml. of dichloromethane. This material, after being dried over $P_2O_5$ at reduced pressure, contained 0.3 mmole of t-butyloxycarbonyl-D-tryptophan per gram of product.

Step B: Preparation of Pyroglu-DPhe-Pro-Phe-Phe-Val-DTrpOCH$_3$

Twenty grams of styrene-2%-divinylbenzene-copolymer-bound Boc-DTrp (0.315 meq DTrp/g) (6.3 mmoles of DTrp) was suspended in 200 ml. of peroxide-free dioxane and equilibrated by being shaken for 1 hour. The solvent was removed by filtration and the material, in a closed mechanical shaker, was washed with 3 × 200 ml. of peroxide-free dioxane for 3-min. intervals. Next the t-butyloxycarbonyl group was removed by treating the product with 2 × 200 ml. of 4N HCl in peroxide-free dioxane containing 2% mercaptoethanol. The duration of the first treatment was 5 min. and that of the second was 30 min. The product was washed with 3 × 200 ml. of peroxide-free dioxane for 3-min. intervals and 3 × 200 ml. of chloroform for 3-min. intervals. Next, the product was treated with 200 ml. of a mixture composed of nine parts of chloroform and one part of triethylamine for 10 min. After washing the product with 3 × 200 ml. of chloroform for 3-min. intervals and 3 × 200 ml. of dichloromethane for 3-min. intervals, 4.10 g. (18.9 mmoles) of Boc-Val in 100 ml. of dichloromethane was added and the mixture was allowed to equilibrate while being shaken for 5 min. Next, 3.9 g. (18.9 mmoles) of N,N-dicyclohexylcarbodiimide in 8 ml. of dichloromethane was added and the reaction was allowed to proceed for 2 hrs. At the end of that time, the product was washed with 3 × 200 ml. of dichloromethane for 3-min. intervals.

The next five amino acids of the product were added by following the above sequence exactly for each amino acid addition. In this manner, 5.01 g. (18.9 mmoles) of Boc-Phe, 5.01 g. (18.9 mmoles) of Boc-Phe, 4.07 g. (18.9 mmoles) of Boc-Pro, 5.01 g. (18.9 mmoles) of Boc-DPhe and 2.44 g. (18.9 mmoles) of LPyroglu were reacted sequentially. For the addition of the latter amino acid, it was necessary to use a mixture of 1 part of dimethylformamide and 6 parts of dichloromethane rather than dichloromethane alone.

The completed polymer-bound polypeptide was washed with 200 ml. of methanol for 5 min., 200 ml. of acetic acid for 15 min., 3 × 200 ml. of methanol for 5-min. intervals, and 3 × 200 ml. of dichloromethane for 5-min. intervals. After the product was dried under reduced pressure, it (22.1 g.) was stirred in a mixture of 800 ml. of methanol and 5 ml. of triethylamine overnight. The mixture was filtered, and the filtrate was concentrated and dried under reduced pressure yielding 4.06 g. of Pyroglu-DPhe-Pro-Phe-Phe-Val-DTrpOCH$_3$, $R_f$ 0.54 ($CHCl_3$-$CH_3OH$-$H_2O$ 90:10:1) on silica gel thin layer.

Step C: Preparation of Pyroglu-DPhe-Pro-Phe-Phe-Val-DTrp

A solution of 4.06 g. of Pyroglu-DPhe-Pro-Phe-Phe-Val-DTrpOCH$_3$ in 40 ml. of $CH_3OH$ was treated with 20.0 ml. of 1.00N NaOH at room temperature. After 1 hr., the mixture was neutralized with 20.0 ml. of 1.00N HCl, and the product was isolated by extraction with $CHCl_3$. The $CHCl_3$ extract was dried over $MgSO_4$ filtered and concentrated under reduced pressure yielding 4.0 g. of Pyroglu-DPhe-Pro-Phe-Phe-Val-DTrp, $R_f$ 0.16 ($CHCl_3$-$CH_3OH$-$H_2O$ 90:10:1) on a silica gel thin layer. A hydrolyzate of the product showed the following amino acid composition expressed in terms of $\mu$moles/mg.: Glu 1.0; Phe 3.29; Pro 1.13; Val 1.16; Trp 1.14.

Employing the procedure of Example 1, but substituting for the LPyroglu used in Step B thereof, an equal amount of DPyroglu, there is produced in sequence, DPyroglu-DPhe-Pro-Phe-Phe-Val-DTrpOCH$_3$ and DPyroglu-DPhe-Pro-Phe-Phe-Val-DTrp.

EXAMPLE 2

Pyroglu-DPhe-Pro-Phe-Phe-Val-DLeu

Step A: Preparation of polymer-bound t-butyloxycarbonyl D-leucine

Fifteen grams of chloromethylated styrene-2% divinylbenzene copolymer (1.92 meq Cl/g; 29 meq) was suspended in 130 ml. of anhydrous, peroxide-free tetrahydrofuran and stirred while a solution of 6.7 g. (29 meq) of t-butyloxycarbonyl D-leucine in 20 ml. of anhydrous, peroxide-free tetrahydrofuran was added. After the mixture was stirred for 1 hr. at room temperature, 2.63 g. (3.6 ml; 26 meq) of triethylamine was added and the mixture was heated under gentle reflux for 24 hrs.

The polymer-bound t-butyloxycarbonyl-D-leucine was isolated by filtration and washed for 5 to 15-min. intervals with 3 × 150 ml. of tetrahydrofuran; 3 × 150 ml. of ethanol; 1 × 150 ml. of acetic acid; 3 × 150 ml. of water; 3 × 150 ml. of methanol; and 3 × 150 ml. of dichloromethane. This material, after being dried over $P_2O_5$ at reduced pressure contained 0.27 mmole of t-butyloxycarbonyl-D-leucine per gram of product.

Step B: Preparation of Pyroglu-DPhe-Pro-Phe-Phe-Val-DLeu

Ten grams of styrene-2%-divinylbenzene-copolymer-bound Boc-DLeu (0.564 meq DLeu/g) (5.64 mmoles DLeu) was suspended in 100 ml. of peroxide-free dioxane and equilibrated by being shaken for 1 hour. The solvent was removed by filtration, and the material in a closed mechanical shaker was washed with 3 × 100 ml. of peroxide-free dioxane for 3-min. intervals. Next, the t-butyloxycarbonyl group was removed by treating the product with 2 × 100 ml. of 4N HCl in peroxide-free dioxane for a 5-min. interval and a 30-min. interval. The product was washed with 3 × 100 ml. of peroxide-free dioxane for 3-min. intervals and 3 × 100 ml. of chloroform for 3-min. intervals. Next, the product was treated with a mixture of 90 ml. of chloroform and 10 ml. of triethylamine for a 10-min. period. After the product was washed with 3 × 100 ml. of chloroform for 3-min. intervals and 3 × 100 ml. of dichloromethane for 3-min. intervals, a solution of 3.06 g. (14.1 mmoles) of Boc-Val was added and the mixture was allowed to equilibrate while being shaken for 5 min. Next, 2.9 g. (14.1 mmoles) of N,N-dicyclohexylcarbodiimide in 5.8 ml. of dichloromethane was added and the reaction was allowed to proceed for 2 hrs. At the end of that time, the product was washed with 3 × 100 ml. of dichloromethane for 3-min. intervals.

The next five amino acids of the product were added by following the above sequence for each amino acid addition. In this manner 3.74 g. (14.1 mmoles) of Boc-Phe, 3.74 g. (14.1 mmoles) of Boc-Phe, 3.03 g. (14.1 mmoles) of Boc-Pro, 3.74 g. (14.1 mmoles) of Boc-DPhe and 1.81 g. (14.1 mmoles) of LPyroglu were reacted sequentially. For the addition of the latter amino acid, it was necessary to use a mixture of 1 part of dimethylformamide and 6 parts of dichloromethane in place of dichloromethane alone.

The completed polymer-bound polypeptide was washed with 100 ml. of methanol for 5 min.; 100 ml. of acetic acid for 15 min.; 3 × 100 ml. of methanol for 5-min. intervals, 3 × 100 ml. of dichloromethane for 5-min. intervals and was dried over $P_2O_5$ under reduced pressure.

Nine grams of the resin-bound product was suspended in 100 ml. of cool trifluoroacetic acid and anhydrous hydrogen bromide was bubbled through the suspension for 1.5 hrs. at room temperature. The mixture was filtered and the filtrate was concentrated to a glass in vacuo. The product was taken up in chloroform and precipitated with ether yielding 3 g. of Pyroglu-DPhe-Pro-Phe-Phe-Val-DLeu, $R_f$ 0.22 ($CHCl_3$-$CH_3OH$-$H_2O$ 90:10:1) on a silica gel thin layer. A hydrolyzate of the product showed the following amino acid composition expressed in terms of μmoles/mg.: Glu 1.10; Phe 2.83; Pro 1.03; Val 1.11; Leu 1.10.

Employing the procedure substantially as described in Example 2, Step B, but adding in sequence the N-t-butyloxycarbonyl derivatives of L-valine, L-phenylalanine, L-phenylalanine, L-proline, and D-leucine, there is produced DLeu-Pro-Phe-Phe-Val-Dleu (HBr or TFA salt).

EXAMPLE 3 t-Butyloxycarbonyl-DPhe-Pro-Phe-Phe-Val-DPhe

Step A: Preparation of t-butyloxycarbonyl-DPhe-Pro-Phe-Phe-ValN₃

Fifteen grams of styrene-2%-divinylbenzene copolymer-bound t-Boc-Val (0.445 meq Val/g) (6.675 mmoles of Val) was suspended in 130 ml. of peroxide-free dioxane and equilibrated by being shaken for 1 hour. The solvent was removed by filtration and the material, in a closed mechanical shaker, was washed with 3 × 130 ml. of peroxide-free dioxane for 3-min. intervals. Next, the t-butyloxycarbonyl group was removed by treating the product with 2 × 130 ml. of 4N HCl in dioxane for a 5-min. and then a 30-minute interval. The product was washed with 3 × 130 ml. of peroxide-free dioxane for 3-min. intervals and 3 × 130 ml. of chloroform for 3-min. intervals. Next, the product was treated with 130 ml. of a mixture consisting of nine parts of chloroform and one part of triethylamine for 10 mins. After the product was washed with 3 × 130 ml. of chloroform and 3 × 130 ml. of dichloromethane for 3-min. intervals, 4.43 g. of t-Boc-Phe (16.7 mmoles) in 123 ml. of dichloromethane was added, and the product was allowed to equilibrate while being shaken for 5 min. Next, 3.45 g. (16.7 mmoles) of N,N-dicyclohexylcarbodiimide in 7 ml. of dichloromethane was added and the reaction was allowed to proceed for 2 hrs. At the end of that time, the product was washed with 3 × 130 ml. of dichloromethane for 3-min. intervals.

The next three amino acids of the product were added by following the above procedure exactly for each amino acid addition. In this manner, 4.43 g. (16.7 mmoles) of t-Boc-Phe, 3.59 g. (16.7 mmoles) of t-Boc-Pro, and 4.43 g. (16.7 mmoles) of t-Boc-DPhe were reacted sequentially.

The completed polymer-bound polypeptide was washed with 2 × 100 ml. of methanol for 5 min., 1 × 100 ml. of acetic acid for 5 min., 4 × 100 ml. of methanol for 5-min. intervals, and 4 × 100 ml. of dichloromethane for 5-min. intervals. Finally, the product was dried over $P_2O_5$ under reduced pressure.

A 3-g. portion of the resin-bound t-Boc-DPhe-Pro-Phe-Phe-Val (1.33 mmoles) was suspended in 30 ml. of purified N,N-dimethylformamide and treated with 30 ml. of anhydrous hydrazine. After the mixture was stirred at room temperature for 2 hours, it was filtered, and the filtrate was concentrated to dryness under reduced pressure. The product was taken up in chloroform, and the solution was washed with water, dried over $MgSO_4$, filtered and concentrated under reduced pressure, yielding 685 mg. of t-Boc-DPhe-Pro-Phe-Phe-ValNHNH₂.

A solution of 480 mg (683 μmoles) of t-Boc-DPhe-Pro-Phe-Phe-ValNHNH₂ in 6 ml. of purified N,N-dimethylformamide was cooled to −10 to −30°C. and stirred while 450 μl of 5N HCl in tetrahydrofuran was added to bring the pH of the solution to 1.3. Next, 70 μl of isoamyl nitrite was added and after 5 minutes the solution was tested for the presence of excess nitrite using starch-potassium iodide paper. Isoamyl nitrite was then added in 10 μl portions until a positive test for nitrite was obtained after a 5-min. interval.

Step B: Preparation of t-butyloxycarbonyl-DPhe-Pro-Phe-Phe-Val-DPhe

The solution of t-Boc-DPhe-Pro-Phe-Phe-ValN₃ was divided into 1.2 ml. aliquots (96 μmoles). One aliquot was reacted with 88 mg. (408 μmoles) of DPheOCH₃.HCl. The pH of the solution was brought to 8 by the dropwise addition of diisopropylethylamine. The reaction was monitored by thin-layer chromatography and was complete after 48 hours. The reaction mixture was concentrated under reduced pressure, taken up in CHCl₃, washed with 0.1N citric acid, then 5% NaHCO₃, dried over MgSO₄, filtered and concentrated under reduced pressure. The sample was purified by preparative thin-layer chromatography on silica using chloroform-ethyl acetate (4:6) and the desired band was scraped from the plate, (t-Boc-DPhe-Pro-Phe-Phe-Val-DPheOCH₃ at $R_f$ 0.50).

The product was eluted with methanol and the methanol solution was concentrated under reduced pressure. The residue was taken up in chloroform, filtered, and concentrated under reduced pressure. The product was then taken up in 1 ml. of methanol and treated with 0.50 ml. of 0.100 N NaOH. When the hydrolysis was complete as evidenced by thin layer chromatography monitoring, the reaction mixture was neutralized with 0.50 ml. of 0.100 N HCl, concentrated under reduced pressure and dried over $P_2O_5$ under reduced pressure. Finally, the product was taken up in anhydrous methanol, filtered, and concentrated under reduced pressure, and triturated with ether, to yield solid t-butyloxycarbonyl-DPhe-Pro-Phe-Phe-Val-DPhe.

EXAMPLE 4 t-Butyloxycarbonyl-DPhe-Pro-Phe-Phe-Val-DNle

Employing the procedure of Example 3, Step B, but substituting for the $DPheOCH_3 \cdot HCl$ used therein, 74 mg. (408 μmoles) of $D-NleOCH_3 \cdot HCl$, there is produced t-butyloxycarbonyl-DPhe-Pro-Phe-Phe-Val-DNleOCH$_3$ ($R_f$ 0.58) and t-butyloxycarbonyl-DPhe-Pro-Phe-Phe-Val-DNle.

EXAMPLE 5 t-Butyloxycarbonyl-DPhe-Pro-Phe-Phe-Val-D allo-i-Leu

Employing the procedure of Example 3, Step B, but substituting for the $DPheOCH_3 \cdot HCl$ used therein, 74 mg. (408 μmoles) of $D\text{-allo-i-LeuOCH}_3 \cdot HCl$, there is produced t-butyloxycarbonyl-DPhe-Pro-Phe-Phe-Val-D-allo-i-LeuOCH$_3$ ($R_f$ 0.54) and t-butyloxycarbonyl-DPhe-Pro-Phe-Phe-Val-D-allo-i-Leu.

EXAMPLE 6

5-Dimethylamino-1-Naphthalenesulfonyl DPhe-Pro-Phe-Phe-Val-DLeu

Three hundred milligrams of styrene-2%-divinylbenzene copolymer-bound t-Boc-DPhe-Pro-Phe-Phe-Val-DLeu (80 μmoles of peptide) was suspended in 5 ml. of peroxide-free dioxane and equilibrated while being shaken for 30 mins. The solvent was removed by filtration and the material, in a closed mechanical shaker, was washed with 3 × 5 ml. of peroxide-free dioxane for 3-min. intervals. Next, the t-butyloxycarbonyl group was removed by treating the product with 2 × 5 ml. of 4N HCl in dioxane for a 5-min. and then a 30-min. interval. The product was washed with 3 × 5 ml. of peroxide-free dioxane for 3-min. intervals and 3 × 5 ml. of chloroform for 3-min. intervals. Next, the product was treated with 5 ml. of a mixture consisting of nine parts of chloroform and one part of triethylamine for 10 mins. After the product was washed with 3 × 5 ml. of chloroform and then 3 × 5 ml. of dichloromethane for 3-min. intervals, a solution of 135 mg. (500 μmoles) of 5-dimethylamino-1-naphthalenesulfonyl chloride in 5 ml. of dichloromethane was added, and the mixture was shaken for 2.5 hrs. At the end of the first hr., 10 mg. of triethylamine in 1 ml. of dichloromethane was added. At the end of the reaction period, the mixture was filtered and the resin-bound product was washed with 3 × 5 ml. of dichloromethane for 3-min. intervals. The resin-bound product was suspended in 2 ml. of trifluoroacetic acid and anhydrous hydrogen bromide was bubbled through the suspension for 2 hrs. The mixture was filtered, and the filtrate was concentrated to dryness. The product was triturated with ether and isolated by filtration yielding 55 mg. of 5-dimethylamino-1-naphthalenesulfonyl-DPhe-Pro-Phe-Phe-Val-DLeu: $R_f$ 0.26 on silica using chloroform-methanol-water (90:10:1).

Employing the procedure substantially as described in Example 6, but substituting for the 5-dimethylamino-1-naphthalenesulfonyl chloride, equimolar amounts of indole-3-acetyl chloride or isovaleryl chloride, there are produced respectively:

indole-3-acetyl-DPhe-Pro-Phe-Phe-Val-DLeu, and isovaleryl-DPhe-Pro-Phe-Phe-Val-Dleu.

EXAMPLE 7

D-Glucuronyl-DPhe-Pro-Phe-Phe-Val-DLeu

An 813-mg. sample of styrene-2%-divinylbenzene copolymer-bound t-Boc-DPhe-Pro-Phe-Phe-Val-DLeu (217 μmoles) was treated in the same manner as described in the above procedure to remove the t-butyloxycarbonyl blocking group and after the washing procedures were completed, 42 mg. (217 μmoles) of D-glucuronic acid in 10 ml. of dichloromethane was added. After the mixture was shaken for 5 minutes, 45 mg. (217 μmoles) of N,N-dicyclohexylcarbodiimide in 0.1 ml. of dichloromethane was added and the reaction was allowed to proceed for 2 hrs. The mixture was filtered and the resin-bound product was washed with 3 × 10 ml. of dichloromethane for 3-min. intervals, 3 × 10 ml. of methanol for 5-min. intervals, 1 × 10 ml. of acetic acid for 10 min., 3 × 10 ml. of methanol for 5-min. intervals, and 3 × 10 ml. of dichloromethane for 5-min. intervals. The resin-bound product was isolated by filtration and dried under reduced pressure. The polypeptide was liberated by suspending the polymer-bound product in 10 ml. of trifluoroacetic acid and passing anhydrous hydrogen bromide through the suspension for 1.5 hrs. The mixture was filtered; the filtrate was concentrated to dryness, and the product was isolated by trituration with ether followed by filtration. The D-Glucuronyl-DPhe-Pro-Phe-Phe-Val-DLeu isolated had an $R_f$ of 0.34 on silica thin layer developed with chloroform-methanol-water (90:10:1).

EXAMPLE 8

Cholyl-DPhe-Pro-Phe-Phe-Val-DLeu

This analog was prepared in precisely the same manner as described for the D-glucuronyl analog. In this instance, 300 mg. of the polymer-bound t-Boc-DPhe-Pro-Phe-Phe-Val-DLeu (80 μmoles) was used and washing and reaction solution volumes were kept at 5 ml. At the acylation step, 98 mg. (240 μmoles) of cholic acid and 63 mg. (240 μmoles) of N,N-dicyclohexylcarbodiimide were used. The Cholyl-DPhe-Pro-Phe-Phe-Val-DLeu obtained had an $R_f$ of 0.33 on a silica thin-layer developed with chloroform-methanol-water (90:10:1).

EXAMPLE 9

2-Depoxy-2-Acetamidoglucopyranosyl DPhe-Pro-Phe-Phe-Val-DLeu

A 500-mg. sample of styrene-2% divinylbenzene copolymer-bound t-Boc-DPhe-Pro-Phe-Phe-Val-DLeu (133 μmoles) is treated in the same manner as described in Example 6 to remove the t-butyloxycarbonyl group and after washing procedures are complete, 54 mg. (133 μmoles) of 3,4,6-tri-O-acetyl-2-deoxy-2-acetamidoglucopyranosyl bromide in 8 ml. of dichloromethane is added along with 15 mg. of triethylamine and the mixture is shaken gently in a closed mechanical shaker overnight. The resin-bound product is isolated by filtration and washed several times with dichloromethane. Next, the product is suspended in a mixture of 20 ml. of methanol and 0.2 ml. of triethylamine and stirred at room temperature overnight. The mixture is filtered and the filtrate is concentrated to a 1-ml. volume. Next, 1.0 ml. of 1.00N NaOH is added and after several hours at room temperature, the mixture is neutralized with 1.0 ml. of 1.00N HCl. The mixture is concentrated under reduced pressure and the product is isolated by extraction with chloroform. After the chloroform solution is washed with water, dried over MgSO₄, filtered and concentrated under reduced pressure, 2-deoxy-2-acetamidoglucopyransoyl-DPhe-Pro-Phe-Phe-Val-DLeu is obtained in an amorphous form.

EXAMPLE 10

(DPhe-Pro-Phe-Phe-Val-DLeu)₂ HBr or Trifluoroacetic Acid Salt

One gram of sytrene-2%-divinylbenzene copolymer-bound t-Boc-DPhe-Pro-Phe-Phe-Val-DLeu (267 μmoles of peptide) was suspended in 10 ml. of purified N,N-dimethylformamide, and 10 ml. of anhydrous hydrazine was added. After the suspension was stirred for 3 hrs., it was filtered, and the filtrate was concentrated under reduced pressure. The residue was taken up in chloroform, and the solution was washed with water, dried over MgSO₄, filtered and concentrated under reduced pressure yielding 215 mg. (244 μmoles) of t-Boc-DPhe-Pro-Phe-Phe-Val-DLeuNHNH₂. The hydrazide was dissolved in 2 ml. of purified N,N-dimethylformamide and the solution was cooled to −10° to −30°C. and stirred. The pH of the solution was adjusted to 1.5 by the addition of 200 μl of 0.5 N HCl in tetrahydrofuran and 25 μl of isoamyl nitrite was added. After 15 mins., the mixture was tested for the presence of excess nitrite using starchpotassium iodide paper, and isoamyl nitrite was added in 5-μl portions until excess nitrite was detected after a 5-min. interval. The temperature of the solution was kept at −10°and 375 mg. of styrene-2%-divinylbenzene copolymer-bound DPhe-Pro-Phe-Phe-Val-DLeu (98 μmoles of peptide) (prepared in the usual fashion from the polymer-bound Boc analog) was added. Next, the pH was adjusted to 7 by the dropwise addition of diisopropylethylamine. The reaction mixture pH was checked occasionally and readjusted to 7 by the addition of diisopropylethylamine. After two days, the polymer-bound product was isolated by filtration and washed with 3 × 10-ml. portions of N,N-dimethylformamide and then 3 × 10-ml. portions of dichloromethane for 5-min. intervals.

The polymer-bound product was suspended in 5 ml. of trifluoroacetic acid and anhydrous hydrogen bromide was bubbled through the suspension for 2 hrs. The mixture was filtered and the filtrate was concentrated to dryness. Trituration of the product with ether, followed by filtration yielded 127 mg. of DPhe-Pro-Phe-Phe-Val-DLeu-DPhe-Pro-Phe-Phe-Val-DLeu (HBr and/or TFA salt) R_f 0.34 on a silica thin layer developed in chloroform-methanol-water (90:10:1).

EXAMPLE 11

(DPhe-Pro-Phe-Phe-Val-DLeu)₃HBr or Trifluoroacetic Acid Salt

Employing the procedures described in Example 9, the polymer-bound t-Boc-DPhe-Pro-Phe-Phe-Val-DLeu-DPhe-Pro-Phe-Phe-Val-DLeu was treated with anhydrous hydrazine to give the corresponding peptide hydrazide. This was converted to the azide by reaction with isoamyl nitrite and then condensed with polymer-bound DPhe-Pro-Phe-Phe-Val-DLeu as before. Treatment with trifluoroacetic acid and hydrogen bromide provides the desired hexapeptide trimer.

EXAMPLE 12

Capsules 10,000 Two-piece hard gelatine capsules for oral use, each containing 250 mg. of one of the active peptides of this invention are prepared from the following ingredient:

|  | grams |
|---|---|
| peptide | 2500 |
| Lactose, U.S.P. | 1000 |
| Starch, U.S.P. | 300 |
| Talc, U.S.P. | 65 |
| Calcium stearate | 25 |

The powdered peptide is mixed with the starch, lactose mixture followed by the talc and calcium stearate. The final mixture is then encapsulated in the usual manner. Capsules containing 10, 25, 50 and 100 mg. of peptide are also prepared by substituting 100, 250, 500 and 1000 gm. for the 2500 gm. in the above formulation.

What is claimed is:
1. A compound of the formula:

W-[X-Pro-Phe-Phe-Y-Z]ₙH or pharmaceutically acceptable acid addition salt thereof, wherein
  n is 1, 2 or 3; W is hydrogen;
    an amino acid residue in the D- or L- configuration selected from pyroglutamyl, prolyl, valvyl, or glycyl;
  indole-3-acetyl;
  isovaleryl;
  dansyl;
  D-glucuronyl;
  t-butyloxycarbonyl;
  cholyl; or 2-deoxy-2-acetamidoglucopyranosyl;
  X is D-phenylalanine;
  Y is L-proline or L-valine; and
  Z is D-leucine, D-tryptophan, D-phenylalanine, D-nor-leucine, D-allo-i-leucine, D-alanine, D-proline or D-valine.

2. The compound of claim 1, wherein n is 1.
3. A compound of claim 1
    W [X-Pro-Phe-Phe-Y-Z]ₙH
wherein
  n is 1, 2 or 3;
  W is D- or L-pyroglutamyl, or t-butyloxycarbonyl;
  X is D-phenylalanine;
  Y is L-proline or L-valine; and
  Z is D-leucine, D-tryptophan, D-phenylalanine or D-nor-leucine.

4. The compound of claim 3, wherein n is 1.
5. The compound of claim 3 of formula:
   Pyroglu-DPhe-Pro-Phe-Phe-Val-D-Trp.
6. The compound of claim 3 of formula:
   Pyroglu-DPhe-Pro-Phe-Phe-Val-DPhe.
7. The compound of claim 3 of formula;
   Pyroglu-DPhe-Pro-Phe-Phe-Val-DLeu.
8. The compound of claim 3 of formula:
   Boc-DPhe-Pro-Phe-Phe-Val-DTrp.
9. The compound of claim 3 of formula:
   Boc-DPhe-Pro-Phe-Phe-Val-DNle.
10. The compound of claim 3 of formula:
   Boc-DPhe-Pro-Phe-Phe-Val-DPhe.

* * * * *